United States Patent
O'Connor

(10) Patent No.: US 11,596,851 B2
(45) Date of Patent: Mar. 7, 2023

(54) APPARATUS AND METHOD FOR LEARNING AND ENHANCING VISUOMOTOR SKILLS

(71) Applicant: Okkulo Limited, Tyne And Wear (GB)

(72) Inventor: Mel David O'Connor, North Tyneside (GB)

(73) Assignee: Okkulo Limited, Tyne And Wear (GB)

( * ) Notice: Subject to any disclaimer, the term of this patent is extended or adjusted under 35 U.S.C. 154(b) by 0 days.

(21) Appl. No.: 16/762,320

(22) PCT Filed: Nov. 9, 2018

(86) PCT No.: PCT/GB2018/053245
§ 371 (c)(1),
(2) Date: May 7, 2020

(87) PCT Pub. No.: WO2019/092431
PCT Pub. Date: May 16, 2019

(65) Prior Publication Data
US 2021/0178245 A1    Jun. 17, 2021

(30) Foreign Application Priority Data
Nov. 9, 2017    (GB) ..................... 1718538

(51) Int. Cl.
A63B 71/04    (2006.01)
A63B 71/06    (2006.01)
(Continued)

(52) U.S. Cl.
CPC ...... *A63B 71/0622* (2013.01); *A63B 24/0062* (2013.01); *A63B 24/0003* (2013.01);
(Continued)

(58) Field of Classification Search
CPC ... A63B 24/062; A63B 71/03; A63B 71/0622; A63B 2225/74
(Continued)

(56) References Cited

U.S. PATENT DOCUMENTS 3,917,264 A    11/1975 Davidson et al.
4,002,893 A *   1/1977 Newcomb .............. A63B 43/06
                                                     473/570

(Continued)

FOREIGN PATENT DOCUMENTS

CN    102657934 A    9/2012
GB      2387786 A    10/2003
(Continued)

OTHER PUBLICATIONS

"Ultraviolet Radiation," Center for Science Education copyright 2017, https://scied.ucar.edu/learning-zone/atmosphere/ultraviolet-uv-radiation (Year: 2017).*
(Continued)

*Primary Examiner* — Alvin A Hunter
(74) *Attorney, Agent, or Firm* — von Briesen & Roper, s.c.

(57) ABSTRACT

An apparatus includes a training area in the form of an enclosed space in which light levels can be controlled, at least one physical element related to a task for which an individual is to be trained, and a lighting arrangement. The lighting arrangement generates a background luminance level in the training area sufficient to cause the vision system of the individual to function in the mesopic or low photopic range of vision, and the physical elements are themselves illuminated by an illumination means. The luminance level of the physical elements is greater than the background luminance level.

15 Claims, 2 Drawing Sheets

(51) Int. Cl.
*A63B 24/00* (2006.01)
*A63B 43/06* (2006.01)
*A63B 67/04* (2006.01)
*A63B 69/00* (2006.01)
*A63B 69/38* (2006.01)

(52) U.S. Cl.
CPC .............. *A63B 43/06* (2013.01); *A63B 67/04* (2013.01); *A63B 69/002* (2013.01); *A63B 69/0015* (2013.01); *A63B 69/38* (2013.01); *A63B 2071/0675* (2013.01); *A63B 2225/74* (2020.08); *A63B 2225/76* (2020.08); *A63B 2243/0025* (2013.01)

(58) Field of Classification Search
USPC .................................................. 473/421, 499
See application file for complete search history.

(56) References Cited

U.S. PATENT DOCUMENTS

| | | | | | |
|---|---|---|---|---|---|
| 4,824,237 | A | * | 4/1989 | Ratner | A61B 5/162 351/203 |
| 4,867,452 | A | * | 9/1989 | Finley | A63B 43/06 473/569 |
| 6,135,456 | A | * | 10/2000 | Cooper | A63B 67/002 273/371 |
| 6,825,056 | B2 | * | 11/2004 | Asakawa | H01L 33/22 257/E33.074 |
| 7,850,514 | B2 | * | 12/2010 | Weber | A63B 69/0053 463/2 |
| 8,257,087 | B2 | * | 9/2012 | Reichow | A63B 69/00 434/247 |
| 8,911,082 | B2 | * | 12/2014 | Ambler | G02C 7/104 351/159.65 |
| 9,233,289 | B2 | * | 1/2016 | Afonshin | A63B 71/0622 |
| 9,248,358 | B2 | * | 2/2016 | Tinjust | G09B 19/0038 |
| 9,511,262 | B1 | * | 12/2016 | DePompe | A63B 69/32 |
| 9,955,551 | B2 | * | 4/2018 | Spero | F21S 4/28 |
| 9,962,570 | B2 | * | 5/2018 | Dallmann | A63B 71/0622 |
| 10,292,246 | B2 | * | 5/2019 | Rajagopalan | G06F 30/13 |
| 10,543,780 | B2 | * | 1/2020 | O'Kell | G09F 13/20 |
| 10,912,976 | B2 | * | 2/2021 | Zimmerman | A63B 71/03 |

FOREIGN PATENT DOCUMENTS

JP 2002028274 A 1/2002
WO WO 2009137667 A1 11/2009

OTHER PUBLICATIONS

International Search Report for Application No. PCT/GB2018/053245; dated Jan. 3, 2019.
International Preliminary Report on Patentability for Application No. PGT/GB2018/053245; dated May 12, 2020.
Japanese Notification of Reasons for Refusal related to Application No. 2020-544176 reported on Oct. 4, 2022. .

* cited by examiner

APPARATUS AND METHOD FOR LEARNING AND ENHANCING VISUOMOTOR SKILLS

CROSS-REFERENCE TO RELATED APPLICATION

This application is a 35 USC § 371 US National Stage filing of International Application No. PCT/GB2018/053245 filed on Nov. 9, 2018 which claims priority under the Paris Convention to the United Kingdom Patent Application No. 1718538.0 filed Nov. 9, 2017.

This invention relates to an apparatus and method for learning and enhancing visuomotor skills.

INTRODUCTION

There are many pursuits in which improved hand-eye or foot-eye co-ordination or improved physical reaction times would improve the performance of the individual involved in the pursuit. For example, in ball sports such as cricket improved hand-eye co-ordination could improve a batsman's ability to play, or hit, a ball, or a fielder's ability to catch or stop a ball. Likewise, for example, in tennis, the ability to react faster with better hand eye co-ordination can improve the percentage of serves returned.

In U.S. Pat. No. 6,364,486, a system is described for training the visual attention capabilities of a subject. For example, the subject is presented with a number of tests that include a central target, a peripheral target and distractor elements. The display time for the targets and elements is held constant. Additionally, the eccentricity of the peripheral targets is held constant for any one test but changed for other tests. The subject is then asked to identify, from a series of potential answers, the correct spatial arrangement of the targets. The parameters of the subsequent tests are then altered, so as to make the test increasingly more difficult, as a subject attains a desired level of success. The system can thereby be used to test and train the subject's visual attention capabilities.

In U.S. Pat. No. 5,812,239, a method and arrangement is described for the enhancement of vision and/or hand-eye co-ordination which involves illuminating light emitting diodes (LEDs) in different sequences, or requiring the subject to extinguish a certain light emitting diode. Specifically, the LEDs are connected to a microprocessor, which illuminates the LEDs in a predetermined manner. A subject is then tasked with following the LEDs, as they illuminate and distinguish, with their eyes, which is tracked by the system and their results, including reaction times, are recorded. Alternatively, a subject may be tasked with touching, in sequence, the LEDs as they illuminate in order to distinguish them. The microprocessor can be used to establish a score for the subject, or indeed pre-programmed with a training regime to improve a subject's visual skills.

WO 01/64005 describes a method and device for influencing the motor-sensory information processing of a user. Such a device includes a screen which is worn over a user's eyes. Visual stimuli are then presented to a user between first and second extreme eye positions. The visual stimuli may be presented in a manner that aims to improve a user's reaction time, or otherwise improve their visual skills.

U.S. Pat. No. 4,824,237 describes a vision and hand/eye co-ordination exercising and testing machine that includes a grid-like array. Each array position is either a lamp position or a dummy position. The machine operates in a number of different modes. In the first mode, the user follows, with their eyes, each lamp position that illuminates. In this mode, the user's ocular muscles are exercised. In a second mode, the user must actively actuate a switch located at each lamp position. In each mode, the sequence in which lamps illuminate, and the position of those lamps within the array, differs. In this way, the user's visual skills and reaction times are improved.

The above known systems and methods seek to improve a subject's visual attention, hand/eye co-ordination and/or reaction times. It is also known, when physically training subjects, for example athletes, to provide a degree of resistance that makes the subject's physical training more difficult.

For example, as discussed in U.S. Pat. No. 5,472,394, a parachute may be attached to an athlete such that when the athlete runs, the parachute creates drag and resistance, thereby making the athlete work harder to improve their fitness. It would be desirable, however, to incorporate physical training with visual training.

This invention seeks to provide an improved apparatus and method for improving hand/eye co-ordination, reaction times and visuomotor skills. More particularly, the invention seeks to improve the above skills as a subject practices for a particular sport.

SUMMARY OF INVENTION

The apparatus of the invention includes illuminating a space with an ambient background level of illumination and with luminous training elements, which together seek to provide a training environment in which the sensory system is forced to work under suboptimal conditions. It seeks to provide a method of training in which the apparatus is used in a manner that permits the learning and/or enhancement of visuomotor skills.

The enhancement produced by the training method of the invention may be related to a number of factors that impact upon one another, including adaptive plasticity of central (cortical) neuronal processes, visuomotor learning, task-specific improved attention and task-specific focus and/or improved visual tracking and improved predictive visual processing (i.e., the main ability to predict the position of a moving object in the future). Two main theories stand behind the training method of the invention and may explain the processes affected by exposure to it.

The first type of theory, which may be termed "adaptive plasticity" posits that the training in the dark gives the performer the opportunity to rehearse the sequence of visuomotor actions required to perform the task under conditions of reduced velocity detection under which stimuli are perceived to move more slowly than normal. Thus, to perform the task successfully, the visuomotor responses to the stimuli must be advanced. Visuomotor skills and performance are then enhanced beyond normal optimal performance levels by adaptive learning and functional (plastic) reorganisation of visuomotor neuronal connections, arising from exposure to the degraded stimulus conditions. Thus, the visuomotor neuromuscular efferent patterns during execution of the movement under the deprived dark conditions are identical (in muscles used) to those used under normal conditions, but speeded up and this speeding up can be transferred to the normal situation to give the impression that the performer has more time to respond. This type of theory explains the acceleration of learning as well as the super-enhancement of visuomotor skills and performance produced by the training method of the invention.

The second type of theory, which may be loosely termed "visual attentiveness" posits that one of the key factors inhibiting training and the acquisition of visuomotor skills in young athletes is the inability to focus, concentrate and exclude distracting information. Consciousness of being on display and being watched by others, of making mistakes and of being ridiculed can all contribute to nervousness and degraded performance. Playing in the dark reduces visual information and forces one to concentrate on the essential core elements. There is much less information about awkward movement or errors and about the facial reactions of others. The athlete may feel invisible or masked. This may enhance the sense of comfort and security and may allow the athlete to enter into a more relaxed state more quickly, which should increase performance; allowing him or her to concentrate on the core elements and their innate creativity. That is, he or she could more quickly acquire the right, professional attitude and be less intimidated by being scrutinised and by peer pressure. Thus, even if playing in the dark has no effect upon adaptive plasticity and optimisation of visuomotor skills per se, it may still help athletes more rapidly achieve optimal performance by reducing anxiety and nervousness and enhancing team identity. In this sense, young athletes, by training in the dark under the conditions established by the apparatus of the invention, may achieve their optimal level in a shorter time.

Novice, accomplished amateur and professional athletes as well as non-athletes can all make use of the training method of the invention. Beginner and novice athletes, who have not yet achieved high or optimal performance levels, can use the technique to accelerate their acquisition of visuomotor skills. That is, it can be used to accelerate the learning curve (reduce the time) that novice (unskilled amateur) players require to achieve improved or optimal performance.

Accomplished and professional athletes, who have already attained high or optimal performance levels, can use the technique to enhance visuomotor skills and performance beyond normal optimal performance levels. That is, it can be used to add a super-optimal dimension or operating range to the learning curve, by changing the neuronal properties of our visuomotor system.

According to one aspect of the invention, there is provided an apparatus as specified in claim 1.

According to another aspect of the invention, there is provided a method of training as specified in claim 20.

BRIEF DESCRIPTION OF THE DRAWINGS

The accompanying drawings illustrate presently exemplary embodiments of the disclose, and together with the general description above and the detailed description below, serve to explain, by way of example only, the principles of the disclosure. In the accompanying drawings.

DETAILED DESCRIPTION

Figure 1:
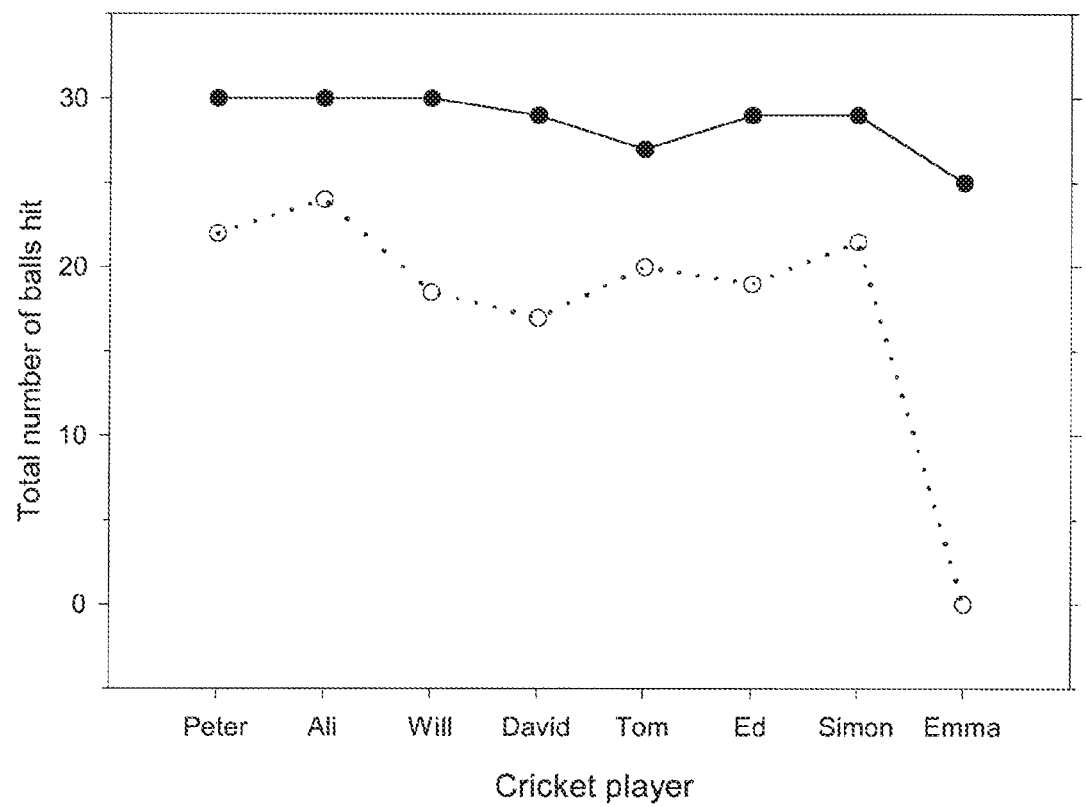
FIG. 1 is a graph showing the pre-training and post-training performance for a group of cricket players.

The apparatus of the invention includes illuminating a space with an ambient background level of illumination, luminous training elements, for example ball trajectory or marker lines, produced either by the fluorescence of coatings illuminated by ultra violet (UV) light, by self-emitting sources of illumination, for example diodes or by other means, and a UV light source. The UV light source may emit light at a wavelength of between 300 to 400 nanometers, between 340 to 380 nanometers, between 370 to 375 nanometers, or preferably at approximately 370 nanometers. In other embodiments, the light emitted may have a wavelength of between 300 to 420 nanometers, and may include purple, or violet, visible light.

An ambient background level is required to stimulate the rod photoreceptors, as well as the cone photoreceptors, of the eye, although cone stimulation alone may be more important for many tasks. Scotopic luminance levels are those at which only the rods, the most sensitive photoreceptors, are operating. Photopic luminance levels are those at which only the cones are operating. Mesopic luminance levels are those at which vision is mediated by the rods and by the cones responding simultaneously to visual stimuli of appropriate spectral compositions and luminance levels. Mesopic vision begins at luminance levels of approximately $10^{-3}$ cd/m$^2$ (i.e. 0.001 cd/m$^2$). The luminance level at which it ends depends to a large extent on the spectral composition of the stimuli viewed, their sizes, and locations of the retina. The rods are fully saturated at luminance levels of 30,000 cd/m$^2$ or 2000 to 5000 scotopic trolands. Rod vision is much slower than cone vision, but cone vision slows down substantially as the light level is decreased from high photopic to low mesopic levels. The training techniques of the present invention, particularly for central vision where rods are absent, are dependent on the light levels being low for cones, and thus cone vision being slow. These lower light levels may be as high as 200 cd/m$^2$ where cones only operate.

The luminance levels, specifically the background luminance levels, may be sufficient to cause the vision system of an individual to function in the mesopic range of vision. Additionally, or alternatively, the luminance levels may be sufficient to cause the vision system of an individual to function in the low photopic range of vision.

In some aspects, the luminance levels defined for ambient background level range from approximately 0.001 cd/m$^2$ to approximately 200 cd/m$^2$.

In some aspects, the luminance levels defined for the ambient background level range from approximately 0.001 cd/m$^2$ to approximately 100 cd/m$^2$.

In some aspects, the luminance levels defined for the ambient background level range from approximately 0.001 cd/m$^2$ to approximately 30 cd/m$^2$, or 1000 to 2000 scotopic trolands.

It may be preferable that the luminance levels defined for the ambient background level range from approximately 0.001 cd/m$^2$, that is, the lower limit of mesopic vision, to an upper limit of approximately 10 cd/m$^2$ or approximately 100 trolands. It may also be preferable for the upper limit to be approximately 200 cd/m$^2$ or approximately 2500 trolands. Although the rod photoreceptors will saturate and will no longer be contributing importantly to vision, cone vision will still be much slower than at normal daylight levels. In general, the ambient background lighting level used in the apparatus of the invention will be between 1.0 and 200 cd/m$^2$, or more specifically between 1.0 and 10 cd/m$^2$, which may be considered the lowest levels at which the method of the invention can be conceivably played and produce the desired psychological conditions of playing in the dark.

The luminance levels defined for the objects of interest, for example the luminous cricket ball or football when training, must be bright enough to be seen by the cones, so they must be above the lower limit of mesopic vision. That is, they may be above approximately $10^{-3}$ cd/m$^2$, or substantially higher. If they are too bright, there will be considerable light scatter in the darkness, which will undesirably raise the ambient luminance level.

A representative example of the core elements of the apparatus of the invention, used in a training procedure developed to enhance the visuomotor skills of young athletes playing football in a 5-a-side (indoor) playing hall, is discussed below, in relation to Table 1.

In this procedure, the ambient lighting was produced by high UV-emitting (black light) sources, which emit harmless, long-wavelength UV radiation from 340 to 380 nanometers, with a peak near 370 nanometers, as well as some purplish visible light (Sound Lab UV G007UV Floodlights, powered by a 240 v AC @ 50 Hz supply). Four UV floodlights were appropriately positioned above the sport hall's playing area to provide a uniform radiant distribution. The UV light causes fluorescent material, including clothing, footwear and painted marker lines, to retro-reflect and emit visible light that stimulates both rods and cones. Team players wore a full-length white strip with either a fluorescent orange, yellow, blue or green bib. White footwear (trainers) were worn. Goal posts and boundary line markers were produced by fluorescent blue paint (ROSCO Invisible Blue #SPF 5785), which is clear under normal light and fluoresces light blue under UV light. The football had an embedded light emitting diode (LED); the light of which is transmitted through translucent pentagons that constitute half of its surface (Huffy Twilight Lighted Soccer Ball 31002).

As discussed above, the lights used with the present invention may emit light within the range of 300 to 420 nanometers. The light emitted may be UV light. Specifically, the UV light emitted may be within the range of 300 to 400 nanometers. Such emitted light may include purple, or violet, visible light.

In some embodiments, the lights used with the present invention may emit UV light within the range of 340 to 380 nanometers. The UV light emitted may include substantially no purple, or violet, visible light.

The apparatus according to the invention may be enclosed within a housing. That is, the apparatus itself may include a housing which encloses one or more, or alternatively all, of the elements of the apparatus. The housing may take the form of a dome or the like.

Moreover, it may be preferably to include a radiation absorbing coating on the housing. That is, it may be preferable to include a radiation absorbing coating, or a black or super-black coating, on the inner surface of the housing. In this way, the coating absorbs the majority, or substantially all, of the visible light within the housing. One such coating is the Vantablack® coating, supplied by Surrey NanoSystems.

In some embodiments, the apparatus may include a motion capture suit, which is worn by the individual. The motion capture suit allows for a system to track positional markers or features in three dimensions, allowing data to be captured based upon the individual's motion. Such data can be used by the system to determine the performance of the individual, when subject to the apparatus and training method of the invention.

Additionally, the apparatus may include an LED floor, screen, monitor or the like to visually display an individual's performance when subject to the apparatus of the invention. The LED floor, screen, monitor or the like may be included within the housing, or may be included outside of the housing. The LED floor, screen, monitor or the like may display the determined performance of the individual as data is captured using the motion capture suit.

A method of training according to the invention comprises the steps of players undertaking:
 (i) An initial amount of training using the apparatus of the invention to produce the enhancement effect, which is flexible and variable (a representative regime is 1-3 hours per week for 4-8 weeks);
 (ii) An additional amount of training using the apparatus of the invention to ensure that the enhancement effect persists, which is also flexible and variable (a representative regime is 2-4 hours a month; and
 (iii) Modifying the training regime to enhance a particular criterion sport task.

EXAMPLES

Evidence supporting claims for the effectiveness of the training technique of the invention is diverse and includes rigorous scientific and statistical evidence.

Of various forms of evidence, rigorous experimentation, defined in terms of the effects of the training technique upon performance, is the most appropriate and approved vehicle for evaluating performance-enhancing techniques. Experimental evaluation took two directions: (1) research designed to establish that the training technique is effective in enhancing the performance of visuomotor skills in different, representative sports (e.g. football, cricket and table tennis); and (2) research designed to determine the physical practice that, on average, best enhances the visuomotor skill acquisition and maintenance.

In both groups of experiments, it is crucial that the testing as well as the training should bear a close relation to the actual task to which generalisations is desired (i.e. performance in sport activities). This is because, according to the long-standing principle of specificity of motor skills (Henry, 1968), the visuomotor training must be very similar to the actual task if transfer is to occur. It is also important that the assessment method be chosen to provide reliable, sensitive measures of performance. Instead of mere subjective performance ratings, objective, quantitative, scoring on interval and ratio scales, which can be statistically analysed, is preferred. Finally, it should be pointed out that the benefits of experimental evidence derive primarily from the general approach rather than from any particular experiments.

(1) Specific Tests of Visuomotor Enhancement

Experiments on skill acquisition are variants of a research design that employs groups of subjects randomly selected from a homogenous population, after being equated on initial levels of performance. These groups are (1) visual training according to the invention in the dark (experimental group); (2) visual training in the normal (lighted) environment (control group)—this is the most appropriate control in which the subjects participate in the same number of practice training sessions as the experimental group; and (3) no specific training (control). The performances, before (pretraining) and after (post-training), of the subjects who receive the training are compared with that of those in the control groups who have received a similar training or no training, to determine whether their performance scores differ as a result of the practice condition administered. Three scientific studies of skill enhancement resulting from the invention have been undertaken with three different groups of young athletes: young footballers (soccer players) and two groups of cricket players. In all three studies, the experimental groups benefited from the training procedures of the invention and showed impressive or extraordinary improvements in performance.

1. Young Footballers

Twenty young footballers, between 8 and 9 years of age, were randomly assigned to the experimental and control (normal) training conditions on the basis of a pre-training evaluation, known as The Johnston SUPAskills Test, marketed under the name Supaskills®, a football skill measurement and rating system (see http://www.supaskills.com). SUPAskills® has been endorsed by Federation Internationale de Football Association (FIFA) and the English Premier League, as a means of rating team players and of evaluating young players. The SUPAskills® evaluation technique comprises 100 standardised measurements of every different skill associated with football. Distance, speed, time and accuracy are assessed for ten predetermined and repeated drills, including juggling, dribbling, passing, swerving, heading, volleying, penalties, dead ball, turn and shoot, and chipping. Sets of scores for each drill are totaled to give a final score and STATS (Skills and Time+ Accuracy=Total & Statistics).

Each of the experimental and control group consisted of 10 players. During training, in both the experimental and control conditions, players were grouped into two opposing teams of five players each (known as 5-a-side). The control group was essential to establish that the players did not improve merely from the result of a training protocol per se, but rather that of the training conditions of the invention.

The players trained for 3 hours a week (on 3 separate days) for 4 weeks. Training took place in a 5-a-side indoor playing hall. Before beginning and after completing training, individual player performance was assessed by a SUPAskills® evaluation.

Table 1 below provides a representative example of the core elements of the apparatus of the invention used in a training procedure developed to enhance the visuomotor skills of young athletes playing football in a 5-a-side indoor playing hall. The luminous values, in $cd/m^2$, for each of the core elements used in a football training model, in both the experimental and control groups, are shown in Table 1 below.

TABLE 1

A representative example of the core elements of the apparatus of the invention

| Object | Condition due to apparatus of the invention | Control condition |
| --- | --- | --- |
| Luminous ball (bright patch) | 0.160 | 14.030 |
| Normal ball | 0.007 | 22.780 |
| Orange marker half-field lines | 0.160 | 15.360 |
| White marker side lines | 0.477 | 12.960 |
| White goal lines | 0.367 | 15.090 |
| White goal post top | 0.606 | 32.440 |
| Orange target in goal | 0.026 | 10.030 |
| Light yellow wall | 0.008 | 13.530 |
| Orange penalty spot | 1.310 | 18.870 |
| Centre spot | 0.332 | 12.810 |
| Player's jersey (green) Centre of field | 0.380 | 7.544 |
| Player's jersey (green) Side of field | 1.350 | 6.473 |
| Player's jersey (orange) Centre of field | 0.530 | 9.581 |
| Player's jersey (orange) Side of field | 1.500 | 7.686 |

In the experimental group, ambient lighting was produced by high UV emitting (black light) sources, which emit harmless, long wavelength UV radiation within the range of 340 to 380 nanometers, with a peak near 370 nanometers, as well as some visible light in the purple region generated by Sound Lab UV G007UV Floodlights, powered by a 240 v AC @ 50 Hz supply. Four UV floodlights were appropriately positioned above the sport hall's playing area to provide a uniform radiant distribution. The UV light causes fluorescent material, including clothing, footwear and painted marker lines, to retro-reflect and emit visible light that stimulates both rods and cones. Team players wore a full-length white strip with either a fluorescent orange, yellow, blue or green bib. The bibs were supplemented with battery-powered LED lights for easier team identification. White footwear in the form of trainers were worn. Goal posts and boundary line markers were produced by fluorescent blue paint (ROSCO Invisible Blue 5785), which is clear under normal light and fluoresces light blue when subjected to UV light. The football has an embedded LED, the light of which is transmitted through translucent pentagons that constitute half of its surface (Huffy Twilight Lighted Soccer Ball 31002).

Individual player performance, assessed before beginning and after completing the 4-week training period, was compared by a two-way analysis of variance statistical model (ANOVA). This is a robust test for statistical significance between the training session and the control (i.e. without training) session.

The ANOVA model utilises an F-ratio and, when the F-ratio is large enough to be significant at typically the 5% or 1% level, it indicates that the difference is unlikely to be caused solely or merely by probable variation. Instead, if the F-ratio is significant, the difference is more likely to be owing to a real and significant difference between the experimental or training condition and the normal or control condition. In other words, if the F-ratio is significant, the training in the dark can be seen as having a positive, beneficial influence upon performance. Additionally, this is paired with Student's t-test, which assesses whether the means of the experimental and control groups are statistically different from each other. The significance was set at $P<0.05$. The differences between the experimental and control groups were not statistically significant, but there was a tendency for the experimental group to show greater improvement in evaluation under the post-training SUPAskills® evaluation technique. The lack of a significant effect can be explained in part by the young age and the day-to-day variation in performance of the young players.

2. Cricket Players

In a first study involving university age cricket players, 8 cricket players received training using the apparatus and method of the invention. This involved practicing batting, under light conditions established by the apparatus of the invention, with a cricket bowling machine. The training lasted for a period of eight weeks and consisted of two sessions a week, each session lasting 2 hours (16 sessions in total). All 8 of the players showed improvement in batting. Their batting improved on average by 33% and the performance enhancement was attributed to the visual training in the dark.

Performance measures of the experimental group were examined before, during and immediately following the 8 week training period. The batting performance of each cricket player was monitored, and the total number of balls hit by each player was recorded. The results are shown in FIG. 1, where the circles and dotted lines show batting performance pre-training, and the solid circles and solid lines show batting performance post-training.

The balls were bowled at each cricket player by the cricket bowling machine at a velocity within the range of 74-90 mph. Relative to a pre-training baseline (circles with dotted lines), all players showed a highly significant increase in their batting performance in terms of the total number of balls that they hit. The statistics for the results shown in FIG. 1 can be found in Table 2 below. The results shown are highly statistically significant.

TABLE 2

Statistics for the results shown in FIG. 1

| T-value | 5.043 |
|---|---|
| p-value | <0.001 |
| Degree of freedom (df) | 7 |

Figure 2:
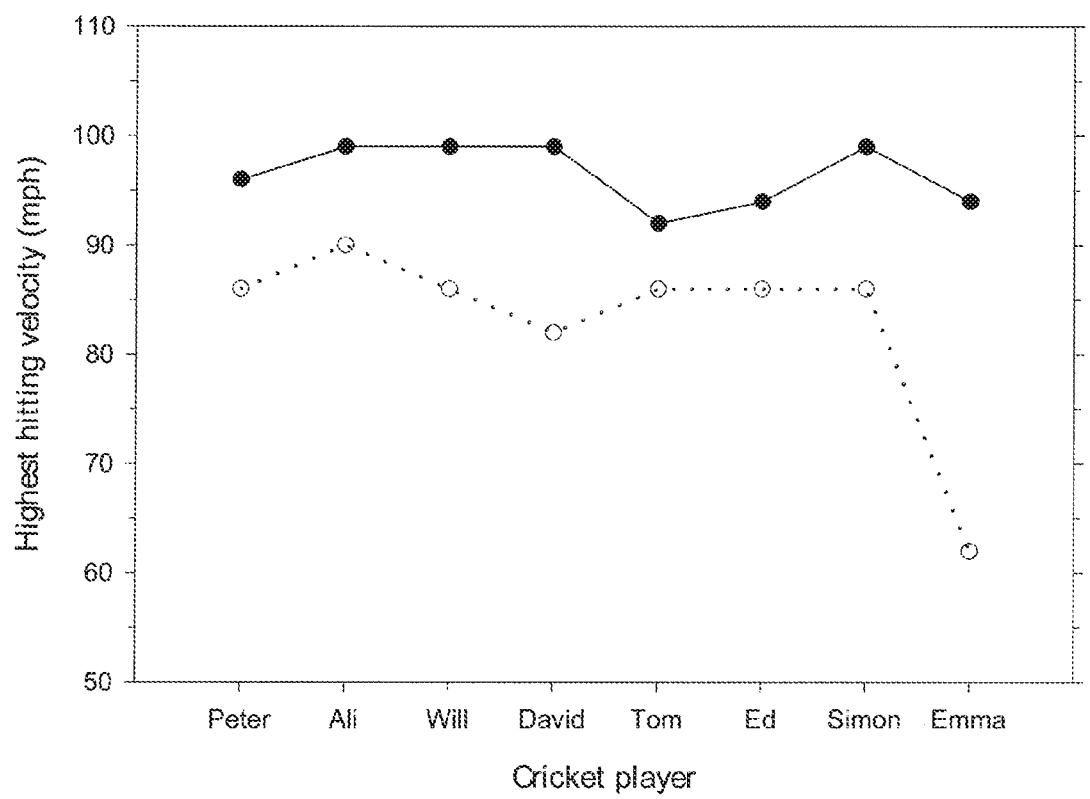
FIG. 2 is another graph showing the pre-training and post-training performance for a group of cricket players.

With reference to FIG. 2, all players also showed an improvement in terms of the highest velocity at which they could hit a predetermined number of balls. The predetermined number of balls in this case was at least 3. The statistics for the results shown in FIG. 2 can be found in Table 3 below. Again, the results shown are highly statistically significant.

TABLE 3

Statistics for the results shown in FIG. 2

| T-value | 4.64 |
|---|---|
| p-value | <0.002 |
| Degree of freedom (df) | 7 |

However, there are several problems in interpreting these data as a performance enhancement resulting from visuomotor training. No random assignment was employed and no control group was tested.

In the second study involving university cricket players, some important improvements in experimental design were introduced. The players were divided into an experimental group and a control group. To avoid Hawthorne effects, other than varying training in the dark versus training in the light, all other factors were held constant (e.g. amount of practice, instruction, testing environment and conditions).

The training method of the invention can be used for different types of exercise, sport or activity. It can be primarily used to exercise and enhance the speed and accuracy (including attention, coordination and reaction times) of the visuomotor skills (e.g. eye-to-hand or eye-to-foot) of athletes engaged in recreational activities and amateur or professional sports.

The enhancement is not restricted to a single sport (e.g. football/soccer, cricket, table tennis) or activity, but covers the enhancement of all visuomotor activities involving fast-action visuomotor performance (eye-hand, eye-foot co-ordination, etc.). In fact, it can be applied to any sport in which quick reflexes and reaction times are involved. Further the training method of the invention is capable of strong and robust cross-over effects. That is, training in one type of sport (e.g. table tennis) may bring improvements in others (e.g. tennis). The training method can also be applied to fast recovery after sport injury (rehabilitation) and to learning in the visually, physically and/or mentally disabled.

Thus, it will be appreciated for persons skilled in the art that the above embodiments have been described by way of example only and not in any limiting sense, and that various alterations and modifications are possible without departing from the scope of the invention as defined by the appended claims.

The invention claimed is:

1. An apparatus comprising:
   a training area in the form of an enclosed space in which light levels can be controlled;
   at least one physical element related to a task for which an individual is to be trained, wherein one or more of the at least one physical element is illuminated by a physical element illumination means; and
   a lighting arrangement, wherein the lighting arrangement generates a background luminance level in the training area, wherein the background luminance level is produced by UV light sources, and wherein the lighting arrangement generates a luminance level of one or more of the at least one physical element in the training area, wherein the luminance level of one or more of the at least one physical element is produced by UV illuminated fluorescent material such that one or more of the at least one physical element emits visible light, providing a luminance level of one or more of the at least physical element that is greater than the background luminance level, and wherein the background luminance level is greater than or equal to 0.001 cd/m$^2$.

2. An apparatus according to claim 1, wherein the background luminance level is less than or equal to 30,000 cd/m$^2$.

3. An apparatus according to claim 2, wherein the background luminance level is in the range 0.001 cd/m$^2$ to 200 cd/m$^2$.

4. An apparatus according to claim 3, wherein the background luminance level is in the range 0.001 cd/m$^2$ to 100 cd/m$^2$.

5. An apparatus according to claim 4, wherein the background luminance level is in the range 0.001 cd/m$^2$ to 10 cd/m$^2$.

6. An apparatus according to claim 5, wherein the background luminance level is in the range of 1.0 cd/m$^2$ to 10 cd/m$^2$.

7. An apparatus according to claim 1, wherein one or more of the at least one physical element includes a coating that is luminous when subjected to UV light.

8. An apparatus according to claim 1, wherein one or more of the at least one physical element includes a self-illuminating source of illumination.

9. An apparatus according to claim 1, wherein the luminance level of the physical element is greater than 0.001 cd/m$^2$.

10. An apparatus according to claim 1, wherein the task is a sport task or a game, and the physical elements are elements of the sport or game.

11. An apparatus according to claim 10, wherein the UV light source emits visible light substantially purple in colour.

12. An apparatus according to claim 1, wherein the UV light sources emit long-wavelength UV radiation.

13. An apparatus according to claim 12, wherein the wavelength of the emitted light is between 340 and 380 nanometers.

14. An apparatus according to claim 13, wherein the wavelength of the emitted light is between 370 and 375 nanometers.

15. An apparatus according to claim 14, wherein the wavelength of the emitted light is approximately 370 nanometers.

* * * * *